US008785179B2

(12) United States Patent
Quinn et al.

(10) Patent No.: US 8,785,179 B2
(45) Date of Patent: Jul. 22, 2014

(54) BIOSENSOR AND METHOD

(75) Inventors: John G. Quinn, Dallas, TX (US); Jerry Elkind, Richardson, TX (US)

(73) Assignee: Texas Instruments Incorporated, Dallas, TX (US)

( * ) Notice: Subject to any disclaimer, the term of this patent is extended or adjusted under 35 U.S.C. 154(b) by 1701 days.

(21) Appl. No.: 10/152,745

(22) Filed: May 22, 2002

(65) Prior Publication Data
US 2003/0219822 A1  Nov. 27, 2003

(51) Int. Cl.
C12M 1/34 (2006.01)
G01N 33/53 (2006.01)
G01N 33/553 (2006.01)
G01N 33/543 (2006.01)
B05D 1/18 (2006.01)
C07C 321/02 (2006.01)
C07C 391/02 (2006.01)

(52) U.S. Cl.
CPC ........ G01N 33/54373 (2013.01); *G01N 33/553* (2013.01); *B05D 1/185* (2013.01); *C07C 321/02* (2013.01); *C07C 391/02* (2013.01)
USPC ........................ 435/287.2; 435/7.92; 436/525

(58) Field of Classification Search
CPC ........... G01N 33/54373; G01N 33/553; C07C 321/02; C07C 391/02; C07C 301/00
USPC .......................................... 436/525, 526, 531
See application file for complete search history.

(56) References Cited

U.S. PATENT DOCUMENTS

| 4,452,773 | A | * | 6/1984 | Molday ........................ 424/1.37 |
|---|---|---|---|---|
| 5,240,640 | A | | 8/1993 | Siiman et al. |
| 5,242,828 | A | * | 9/1993 | Bergstrom et al. ......... 435/287.1 |
| 5,981,297 | A | * | 11/1999 | Baselt ........................... 436/514 |
| 6,045,925 | A | | 4/2000 | Klabunde et al. |
| 6,197,515 | B1 | | 3/2001 | Bamdad et al. |
| 6,406,921 | B1 | * | 6/2002 | Wagner et al. ................ 436/518 |
| 6,476,199 | B1 | * | 11/2002 | Salamone et al. ............ 530/405 |
| 6,495,257 | B1 | | 12/2002 | Terase et al. |
| 6,495,328 | B2 | * | 12/2002 | Nakamura et al. ................ 435/6 |
| 6,514,481 | B1 | | 2/2003 | Prasad et al. |
| 6,686,161 | B2 | | 2/2004 | Johnson et al. |
| 7,081,489 | B2 | | 7/2006 | Chen et al. |

OTHER PUBLICATIONS

M. Cygan et al, J. Amer. Chem. Soc. (1998), vol. 120, pp. 2721-2732.*
J. Tour et al, J. Amer. Chem. Soc. (1995), vol. 117, pp. 9529-9534.*
C. Yu et al, J. Org. Chem. (1999), vol. 64, pp. 2070-2079.*
T. Dunbar et al, J. Phys. Chem. B (2000), vol. 104, pp. 4880-4893.*
F. Fan et al, J. Amer. Chem. Soc. (2002), vol. 124, pp. 5550-5560.*
Kataby et al. Self-assembled monolayer coatings on amorphous iron and iron oxide nanoparticles: thermal stability and chemical reactivity studies. Langmuir 1997, vol. 13, pp. 6151-6158.*

(Continued)

*Primary Examiner* — Shafiqul Haq
(74) *Attorney, Agent, or Firm* — Alan A. R. Cooper; Frederick J. Telecky, Jr.

(57) ABSTRACT

Surface plasmon resonance (SPR) sensor biointerface with a rigid thiol linker layer and/or interaction layer ligand loading with reversible collapse and/or iron oxide nanoparticle sensor response amplification.

5 Claims, 6 Drawing Sheets

(56) References Cited

OTHER PUBLICATIONS

Cao et al. Preparation of amorphous Fe2O3 powder with different particle sizes. J. Mater. CHem 1997, vol. 7, pp. 2447-2451.*

Baselt et al. A biosensor based on magnetoresistiance technology. Biosensors and Bioelectronics 1998, vol. 13, pp. 731-739.*

Edelstein et al. The BARC biosensor applied to the detection of biological warfare agents. Biosensors & Bioelectronics 2000, vol. 14, pp. 805-813.*

X. Cao et al.; Preparation of Amorphous Fe2O3 Powder with Different Particle Sizes, J. Mater. Chem., 1997, pp. 2447-2451.

J. H. Gu et al.; Enhancement of the Sensitivity of Surface Plasmon Resonance Biosensor with Colloidal Gold Labeling Technique; Supramolecular Science 5; pp. 695-698, 1998.

Stefan Lofas et al.; Methods for Site Controlled Coupling to Carboxymethyldextran Surfaces in Surface Plasmon Resonance Sensors; Biosensors & Bioelectronics; pp. 813-822, vol. 10, 1995.

Joydeep Lahiri et al.; Strategy for the Generation of Surfaces Presenting Ligands for Studies of Binding Based on an Active Ester as a Common Reactive Intermediate: A Surface Plasmon Resonance Study; Analytical Chemistry, vol. 71, No. 4, Feb. 15, 1999; pp. 777-790.

Jiri Homola et al.; Surface Plasmon Resonance Sensors; Sensors and Actuators B 54 (1999); pp. 3-15.

Rebecca J. Green et al.; Surface Plasmon Resonance Analysis of Dynamic Biological Interactions with Biomaterials; Biomaterials 21; pp. 1823-1835, 2000.

Advances in surface plasmon resonance biosensor analysis by Rebecca L. Rich et al., pp. 54-61, 2000.

Magnetic properties of amorphous Iron (III) oxide thin films, Shigeematsu et al., Supplement au Journal de Physique Colloques, vol. 40, 1979.

Amorphous iron oxide prepared by microwave heating by Palchik et al.; p. 2176-2181; J. Mater. Res., vol. 15, No. 10, Oct. 2000.

* cited by examiner

BIOSENSOR AND METHOD

CROSS-REFERENCE TO RELATED APPLICATIONS

The following patent applications disclose related subject matter: Ser. No. 10/152,760, filed May 22, 2002; Ser. No. 10/799,283, filed Mar. 12, 2004; and Ser. No. 11/140,414, filed May 23, 2005. These referenced applications have a common assignee with the present application.

BACKGROUND OF THE INVENTION

The invention relates to (bio)chemical sensors, and more particularly to surface plasmon resonance (SPR) sensors and related methods.

Optical sensors for (bio)chemical detection can provide real-time analysis and typically rely on phenomena such as absorption lines, refractive index changes, and specific binding events. A surface plasmon resonance (SPR) sensor measures changes of refractive index in a dielectric biointerface on a thin conductor using the dependence of the surface plasmon wave vector on the refractive index. Thus with a biointerface including specific binding sites for an analyte, the analyte can be detected quantitatively in a fluid contacting the biointerface due to the change in refractive index by addition of the analyte to the biointerface. Green et al, Surface Plasmon Resonance Analysis of Dynamic Biological Interactions with Biomaterials, 21 Biomaterials 1823-1835 (2000) and Homola et al, Surface Plasmon Resonance Sensors: Review, 54 Sensors and Actuators B 3-15 (1999) describe various types for SPR sensors and applications. Useful pairs of analyte and analyte-specific ligand include antibody-antigen, lectin-carbohydrate, receptor-ligand, DNA-DNA, et cetera.

FIG. 6 illustrates a total internal reflection SPR sensor which illuminates a thin (e.g., 50 nm thick) gold sensor film from the inside with light of wavelength about 800 nm and detects the reflected light with a linear photo-diode array. The refractive index of the biointerface (boundary layer) on the outside of the gold sensor film determines the wave vector of surface plasmon waves at the gold-biointerface: the surface plasmon wave decays exponentially in the dielectric biointerface with a 1/e decay distance of roughly 200 nm. The inside illumination of the gold film covers a range of incident angles due to the geometry of the sensor; and for the angle at which the light's wave vector component parallel the gold film matches that of a surface plasmon wave, the illumination will be resonantly absorbed to excite surface plasmon waves. And the linear photodiode array detects the angle at which resonant absorption occurs and, inferentially, the refractive index of the biointerface. Indeed, monitoring the refractive index as a function of time during introduction to the biointerface of a fluid containing an unknown quantity of analyte allows analysis of the reaction of analyte with the specific binding sites in the biointerface.

Various biointerface structures functionalized with specific analyte-binding sites have been proposed: self-assembled monolayer (SAM) assembled from thiols with functionalized tail groups, covalently immobilized derivatized carboxymethyl dextran matrix, streptavidin monolayer immobilized with biotin and functionalized with biotinylated biomolecules, functionalized polymer films, and so forth. For example, U.S. Pat. No. 5,242,828 (Biacore) discloses a gold surface with a SAM linker (barrier) film bound to the gold and with analyte-affinity ligands bound (immobilized) to either the SAM directly or to a hydrogel which, in turn, is linked to the SAM. The SAM units have the structure X—R—Y where X binds to the gold and may be a sulfide, R is a hydrocarbon chain of length 12-30 carbons (e.g., $(CH_2)_{16}$) and preferably without branching for close packing, and Y is —OH which binds to derivatized dextran (the hydrogel). Similarly, Lahiri et al, A Strategy for the Generation of Surfaces Presenting Ligands for Studies of Binding Based on an Active Ester as a Common Reactive Intermediate: A Surface Plasmon Resonance Study, 71 Analytical Chemistry 777-790 (1999), shows SAMs with units having structure X—R—Y with X a sulfide, R a hydrocarbon chain, and Y an ethylene glycol chain. And U.S. Pat. No. 6,197,515 discloses a SAM having unit structure X—R-Ch where Ch is a chelating group which binds a metal ion that, in turn, binds an analyte-affinity ligand (binding partner).

Linking an extended hydrogel to the linker film increases the binding capacity of the surface. For example, derivatized carboxymethyl dextran (molecular weight from 10 to 500 kDa) may be covalently linked to the linker film as in Löfås et al, Methods for Site Controlled Coupling to Carboxymethylated Surfaces in Surface Plasmon Resonance Sensors, 10 Biosensors and Bioelectronics 813 (1995). This hydrogel increases the binding capacity of the surface by as much as 10-fold. It requires charge preconcentration of the ligand into the hydrogel. This is done by suspending the ligand to be immobilized in a low ionic strength buffer at a pH below the isoelectric point of the ligand. The ligand will be positively charged in this buffer and will rapidly accumulate within the negatively charged hydrogel. Pre-activation of the hydrogel matrix by activating a fraction of the carboxyl groups results in efficient coupling of ligand. The most common activation chemistry employs a mixture of N-ethyl-N'-(3-dimethylaminopropyl)carbodiimide hydrochloride (EDC) and N-hydroxysuccinimide (NHS). This produces NHS esters that react with amines (indigenous to most pertinacious ligands), and this is most efficient under basic conditions (e.g. pH 8-9). However, many ligands are acidic and will only become positively charged at very low pH. Therefore, immobilization yields for these ligands are very low to negligible.

SPR-based biosensors monitor the refractive index that results from binding of a target analyte at the biointerface. This refractive index change is proportional to the molecular mass of the target analyte and the number of molecules bound. Hence, for small molecules, or low binding levels, it is sometimes necessary to amplify this primary binding response by using a particle labeled secondary reagent. Gu et al, Enhancement of the Sensitivity of Surface Plasmon Resonance Biosensor with Colloidal Gold Labeling Technique, 5 Supramolecular Science, 695-698 (1998), studies the interaction of Fab' (human IgG fragment) with a mixture of human IgG and sheep anti-human IgG with SPR; Gu enhances the signal by attaching colloidal gold to the sheep anti-human IgG. The SPR sensor has a biointerface made of a 2-mercapto-ethylamine SAM which amide connects to propionate that, in turn, disulfide connects to the Fab'. The colloidal gold particles increase the SPR signal by a factor of up to 300 as the sheep anti-human IgG binds to the Fab'. However, the stability of colloidal gold and other popular colloidal particles is often poor and stabilizers are required. Also linkage of molecules to these particles is commonly complicated with moderate results.

Cao et al, Preparation of amorphous $Fe_2O_3$ powder with different particle sizes, 7 J. Mater. Chem. 2447-2451 (1997) describes extension of Suslick's method of sonication of metal carbonyls to form amorphous iron oxide nanoparticles.

SUMMARY OF THE INVENTION

The present invention provides biointerfaces and SPR sensors plus related methods with one or more of the features of a SAM with rigid units adjacent to the assembly surface, reversible entrapment for ligand loading of an interaction layer, and detection amplification or preconcentration with amorphous iron oxide nanoparticles.

These have advantages including increased SPR sensor detection ease and/or sensitivity.

BRIEF DESCRIPTION OF THE DRAWINGS

The drawings are heuristic for clarity.

DETAILED DESCRIPTION OF THE PREFERRED EMBODIMENTS

1. Overview

Preferred embodiment surface plasmon resonance (SPR) sensors and methods include preferred embodiment biointerface structures and/or ligand loading methods and/or signal amplification methods. In particular, a preferred embodiment biointerface linker film on a metal surface has the structure of a self-assembled monolayer (SAM) formed from compounds with a rigid, roughly linear portion adjacent the metal surface. Suitable compounds are of the structure X—R—Y wherein X is a group such as —S— that binds to gold (or other free electron metal), Y includes functional group(s) for linking (directly or indirectly) ligand(s) which will bind target analyte(s), and R provides a rigid carbon chain backbone which close-packs upon self assembly. For the linker film of FIG. 1, X is —S—, Y is —$CH_2C(CH_2OH)_3$, and R is —$C_6H_4C{\equiv}CC_6H_4C{\equiv}CC_6H_4C{\equiv}CC_6H_4C$—. The conjugated double and triple bonds of R provide the rigidity, and the para connections yield a roughly linear structure. Y provides a bulky, hydrophilic end to form a dense surface with active groups for linking to either ligands or an interaction layer which, in turn, includes ligands. The resulting SAM surface will be composed of tightly packed hydroxyl groups forming an ideal linker film. The stability of the surface chemistry is directly related to the stability of the linker film and is critical to any biointerface applications.

In general, a biointerface may include a hydrogel interaction layer anchored to a SAM linker film or directly to a metal surface and loaded with immobilized ligands. FIGS. 4a-4d illustrate a preferred embodiment reversible entrapment method for loading ligands into such an interaction layer.

Figure 5A:
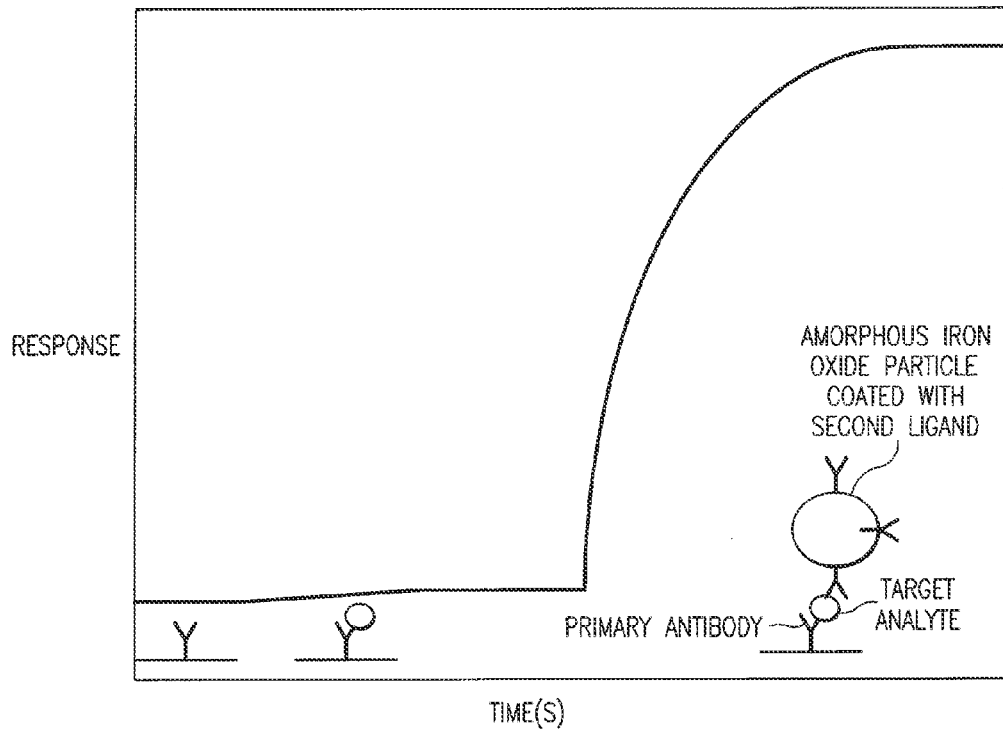
FIGS. 5a-5b illustrate preferred embodiment amplification.
Figure 5B:
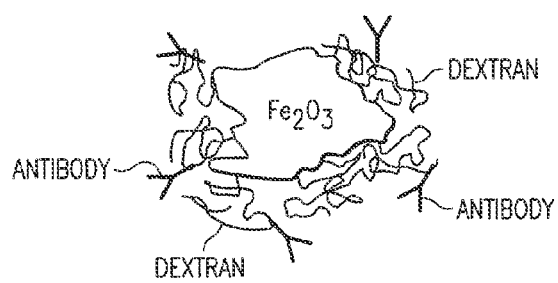

FIGS. 5a-5b show preferred embodiment iron oxide nanoparticle colloid for enhancing SPR response, thereby enhancing the sensitivity of such a biosensor. After binding of available analyte to ligands immobilized in the interaction layer of a biointerface, the introduction of a colloidal suspension of such nanoparticles (precoated with a ligand that binds to the target analyte) will amplify the SPR signal due to the large effect of amorphous iron bound to the biointerface on refractive index. Also, the magnetic properties of the coated ferric oxide nanoparticles permit magnetic separation prior to 2. Self-Assembled Monolayer (SAM)

Figure 1:
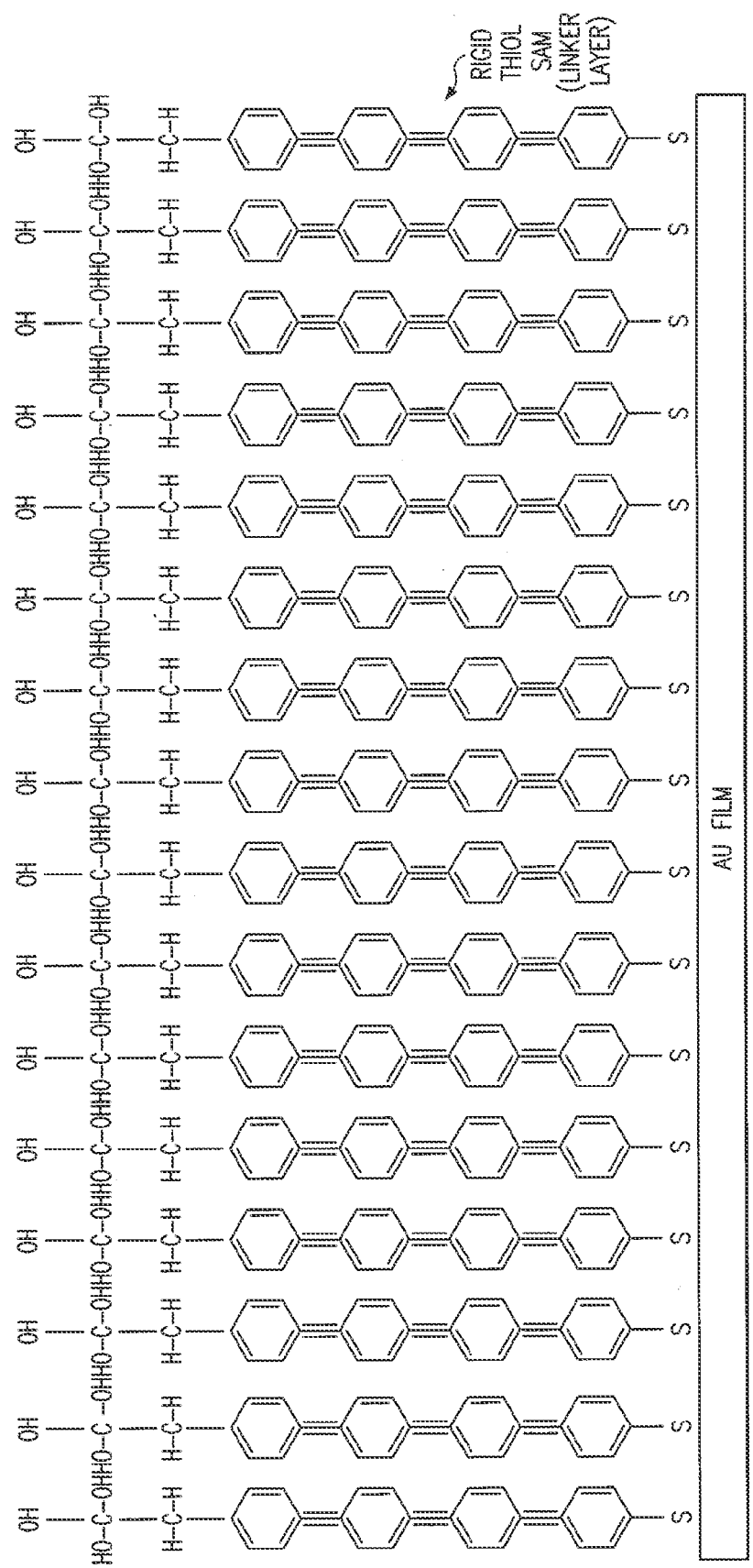
FIG. 1 illustrates in cross-sectional elevation view a first preferred embodiment self-assembled monolayer.

FIG. 1 heuristically illustrates in cross-sectional elevation view a first preferred embodiment self-assembled monolayer (SAM) using thiols with a rigid portion adjacent the thiol group. First preferred embodiment SPR sensors with gold detection surfaces use such a SAM as a linker film that enables direct attachment of the ligand. The SAM may be assembled from rigid thiols such as HS-(Hydrocarbon Ring)$_n$-Y where n may be in the range 1-20 and the head group Y has suitable activatable functional group(s) or active group(s). For example, the rigid thiol of FIG. 1 has a backbone including three phenylethynyl units with the gold-attachment end terminated in a thiobenzene and the other end terminated with a head group of tris(hydroxymethyl)ethane. Of course, during self-assembly on the gold surface, the —SH becomes —S—Au. Alternative rigid carbon chains include anthracene-type and phenanthrene-type (fused aromatic rings) backbone, a steroidal-type (fused non-aromatic rings) backbone, or a mixed structure, all with a thiol termination. The compound used for self-assembly could be a disulfide such as Y—R—S—S—R—Y instead of a thiol, the —S—S— cleaves for attachment to the gold. Further, alternative X bonds to the gold could be —S—S—Au, —Se—Au, . . . , and also more complex sulfur-containing groups such as —COS—Au, —CSS—Au, . . . .

Figure 2:
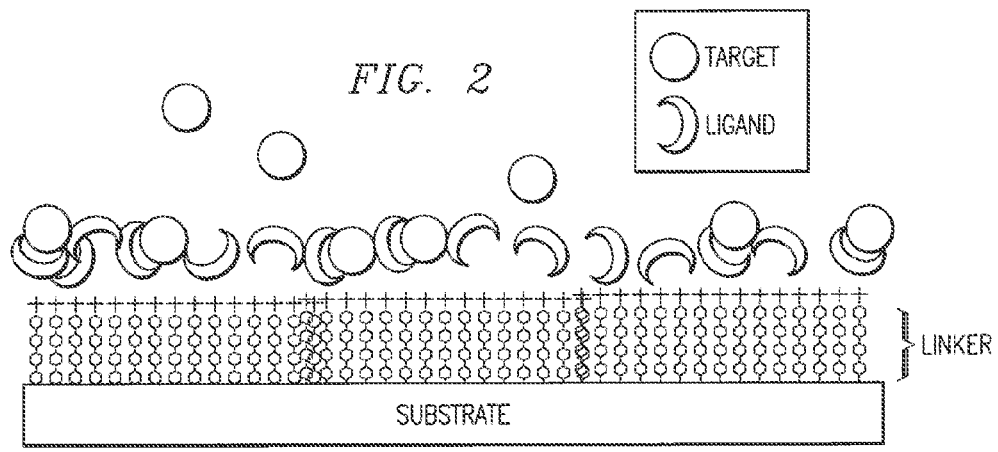
FIG. 2 depicts a functionalized SAM interacting with target analyte.

The resulting SAM's are extremely stable and may be functionalized directly with ligands to form the interaction layer of a biointerface. FIG. 2 heuristically illustrates such an interaction layer with the crescents representing ligands linked to the linker film SAM and circles representing analytes. In this case the interaction layer is very thin (only a single monolayer of ligand), but it is possible to extend this linker film by linking an extended support (e.g. hydrogel) that can anchor a high density of bound ligand to the surface; see FIG. 3.

For the case of ligands directly bound to the SAM, a mixed SAM could be used in which a small fraction (e.g., 5-10%) of the SAM units are longer than the majority of SAM units, and only these longer SAM units contain a head group which binds the ligand. The extra length could be either a longer backbone or a longer head group of a combination. The majority of SAM units would have an inactive, hydrophilic head group. Thus the ligands would be spaced on the SAM and extend beyond the majority surface and thereby permit large analytes binding to the ligands without steric hinderence from adjacent ligands. For example, a SAM assembled from a mixture of X—R—Y and X—R—Z where X, R, and Y are as in FIG. 1 and Z is —$(CH_2)_{20}COOH$; or the Y could be hydrophobic such as —$CH_3$ and the Z hydrophilic and active such as —$(CH_2)_{10}(CHOH)_6CH_2OH$. More generally, the two (or more) compounds for self-assembly could be somewhat different: X—R—Y and X'—R'—Y' or one or more asymmetrical precursors such as Y—R—S—S—R'—Y'.

Interchain interactions of the rigid thiols permits close packing to form the SAM and thus preventing oxidation of the thiol-gold bond and ensuring linker film stability. The head group is composed of a cluster of hydroxyl groups which form a hydrophilic surface that resists non-specific binding while also allowing activation and further derivatization for attachment of ligands (FIG. 2) or hydrogels (FIGS. 3 and 4a-4d also showing ligands linked to the hydrogel). Other rigid hydrocarbon ring structures (e.g. steroidal compounds, fused ring chains etc.) may be employed.

Indeed, rigidity of the carbon chain adjacent to the sulfur attachment at the gold surface underlies linker film stability and may be characterized as a carbon chain with no $sp^3$-bonded carbons. Also, rough linearity of the rigid chain helps close-packed assembly. For example, the following classes of rigid carbon chains may be used.

Figure 7A:
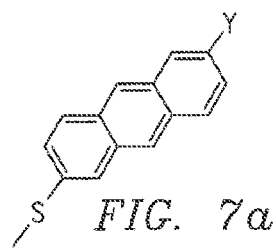
FIGS. 7a-7e are various preferred embodiment chain types.
Figure 7B:
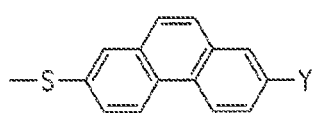

(1) aromatic rings para-connected by linear alkynes, as in FIG. 1.
(2) direct para-connected aromatic rings such as biphenyl; see FIG. 7c.
(3) fused aromatic rings, such as anthracene, phenanthrene, and chrysene; see FIGS. 7a-7b.
(4) fused non-aromatic rings, such as steroid types; see FIG. 7d.
(5) an ethynyl connecting the sulfur to a ring; see FIG. 7e.
(6) combinations of (1)-(5).

The rigid carbon chain should have a length in the range of 6-100 carbon atoms, and preferably in the range 10-50. The length is measured as the shortest string of carbons from X to Y, so traversing a para-connected aromatic ring would count as four carbons.

The first preferred embodiment SAM in FIG. 1 is of class (1) and effectively has a rigid, roughly linear 22-carbon chain with 16 aromatic carbons (four in each of the four rings) and 6 sp carbons (two in each of three —C≡C— connectors). Replacing the —C≡C— groups with trans —CH═CH— groups connecting the rings would somewhat maintain the rigidity and linearity of the carbon chain. The number of carbons in such FIG. 1 rigid carbon chains increases in multiples of 6 starting from 10 (two aromatic rings with one ethynyl between).

Figure 7C:

Biphenyl provides a chain of length 8 carbons; see FIG. 7c. Additional rings increments the length in multiples of 4.

With three fused aromatic rings (anthracene and phenanthrene) the rigid carbon chain would have 7 or 8 carbons, depending upon the —S— and —Y connection locations on the terminal rings; see FIGS. 7a-7b.

Figure 7D:
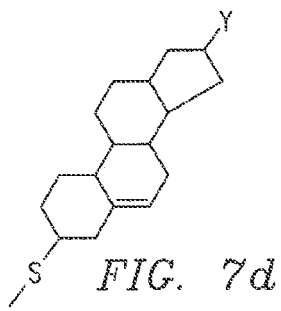
Figure 7E:
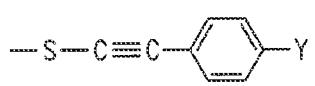

In a FIG. 7d type chain, rigidity against ring flexing arises from the fusing of multiple rings plus, optionally, double bond(s) in some rings. In particular, for a thio-steroid-based SAM the four fused non-aromatic rings (cyclopentyl hydrophenanthrene) provide a 9-carbon chain from the sulfur as in FIG. 7d.

Substitutions such as F or OH in place of H may be made on the rings or the trans —CH═CH— connectors provided the substitutions do not deter close packing of the rigid chains. Further, the rigid chains may be partitioned into two (or more) rigid subchains with a heteroatom or sp³ carbon or larger group connecting the two subchains. For example, a phenyl ether derivative —S—C$_6$H$_4$—O—C$_6$H$_4$—Y has two 4-carbon subchains (each para-connected aromatic ring), and a variant of the rigid chain of FIG. 1 could have a CH$_2$ group inserted to form —S—C$_6$H$_4$C≡CC$_6$H$_4$CH$_2$C≡CC$_6$H$_4$C≡CC$_6$H$_4$—Y with rigid subchains of lengths 11 and 13 (the methylene carbon counts as the terminal carbon in both subchains). The preferred minimum length for the rigid carbon (sub)chain connected to the gold-bonded sulfur (i.e., adjacent the gold) is 8 for a single chain and 6 for a chain with partitions.

The head group may have functional and/or coupling group(s) connected to a separate (non-rigid) carbon chain such as the trishydroymethly ethyl of FIG. 1 or have functional and/or coupling group(s) directly connected to the terminal of the rigid carbon chain. In particular, Y could include a functional group (useful for attaching an interaction layer or a coupling group) such as hydroxyl, amine, carboxyl, thiol, aldehyde, and mixtures thereof, and/or include coupling group(s) (useful for direct coupling of ligands to the SAM) such as N-hydroxysuccinimide ester, reactive imidazole derivatives, epoxy, aldehyde, sulfonyl chlorides, vinyl, divinylsulfone, halogens, maleimide, disulfides, thiols, and mixtures thereof.

For further example, the tris-hydroxymethyl ethyl head group of the FIG. 1 has its own 3-carbon methyl ethyl backbones ending with bulky, hydrophilic hydroxyl functional groups. Similar head groups could be gem-ethyl diol (—CH$_2$—CH(OH)$_2$), fluoro gem-propyl diol (—(CF$_2$)$_2$—CH(OH)$_2$), ethylamide (—CH$_2$—CONH$_2$), and other such hydrogen-bonding functional groups. Alternatively, the head group could be part of the terminal of the rigid carbon chain, such as a terminal phenol or aniline or analogs: one or more —OH's and/or one or more —NH$_2$'s on the terminal ring. Even embedding one or more O's or N's in a terminal ring which may be a 5-member ring; that is, a terminal such as furan, pyridine, pyrrole, imidazole, quinoline, oxazole, indole, . . . where the ligand bonds to a carbon in the terminal ring or may bond to an embedded N.

In more detail, the first preferred embodiment (FIG. 1) self assembled monolayer (SAM) using hydrocarbon ring-based thiols can be fabricated with the following steps:

(a) The metal (gold) coated surface of a substrate is cleaned by exposure to an oxygen plasma and then a hydrogen plasma for 5 min, respectively.
(b) A 0.1 mM-10 mM solution of the rigid thiol compound is prepared in a suitable solvent system (e.g. dichloromethane, ethanol, hexane etc.), and the cleaned substrates are incubated in the solution for 48 hours at room temperature. Elevated incubation temperature from 30 to 100° C. may improve linker film packing density at the metal surface.
(d) The linker film coated surface is rinsed repeatedly in the solvent used for coating and then in ethanol. The linker-on-metal coated substrates are then stored under nitrogen until required.

3. Interaction Layer Loading Method

Figure 3:
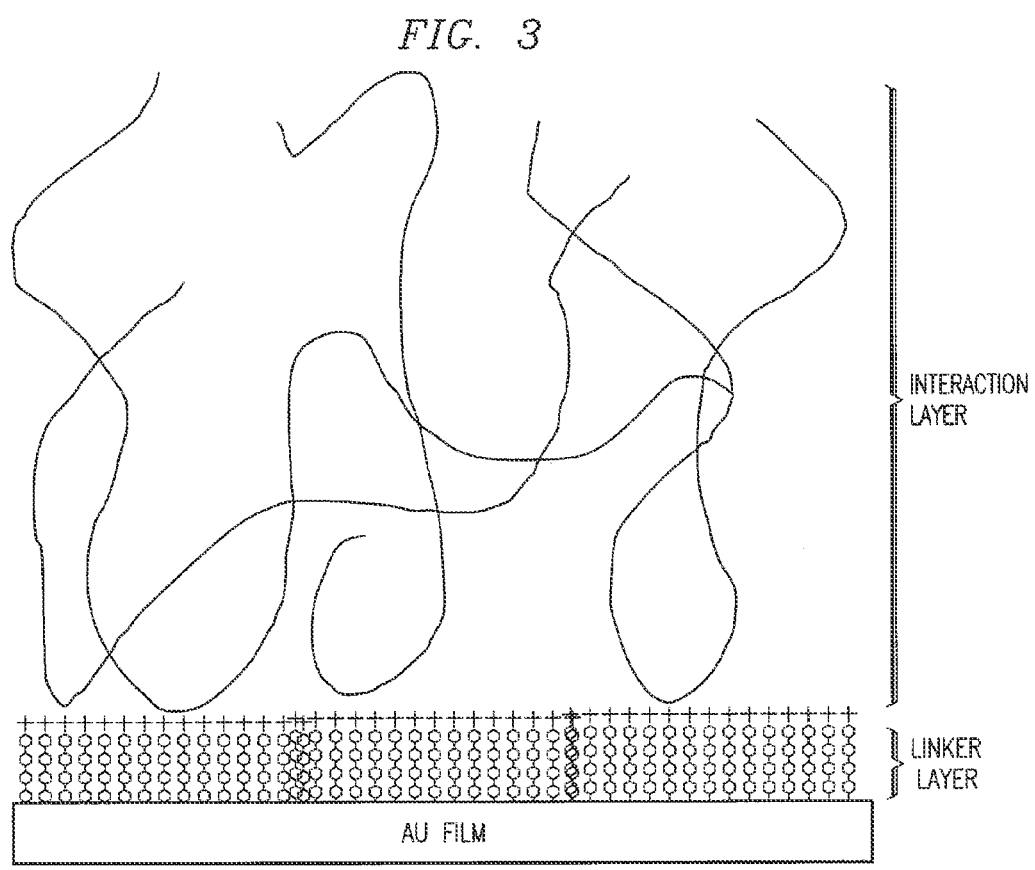
FIG. 3 is a cross-sectional elevation view of a preferred embodiment biointerface and self-assembled monolayer.

At its simplest the interaction film will simply be composed of the ligand attached directly to the SAM. However, the attachment of an extended hydrogel to support higher loading capacity is favored in many applications and is shown in FIG. 3. The hydrogel layer typically is in the range of 5-200 nm thick. The hydrogel can be composed of any hydrophilic polymer which provides high biomolecule loading capacity plus low non-specific binding of molecules such as proteins found in crude samples. High ligand loading capacities are achieved by employing the preferred embodiment ligand loading method which is based on a mechanical entrapment principle.

Figure 4A:
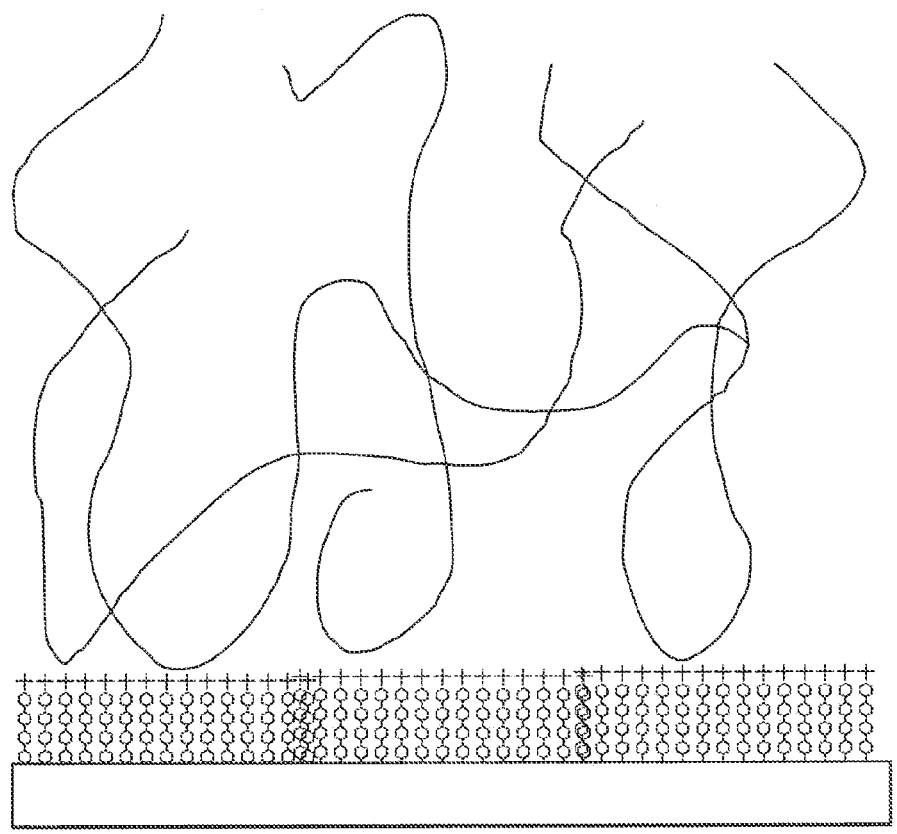
FIGS. 4a-4d show a preferred embodiment ligand linkage method.
Figure 4B:
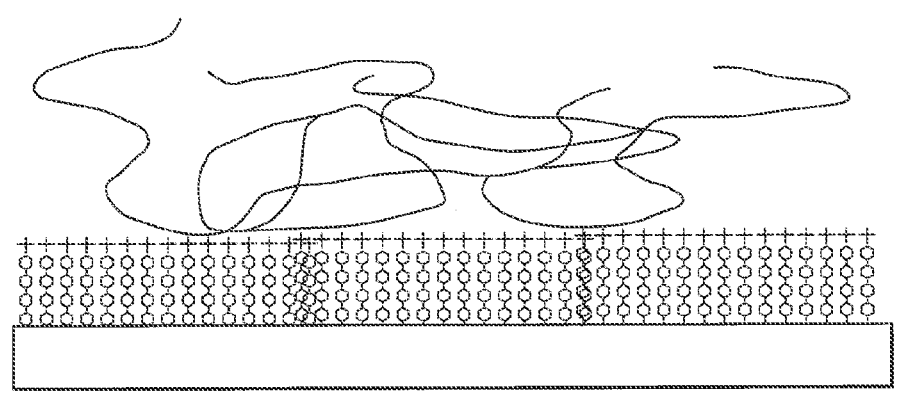
Figure 4C:
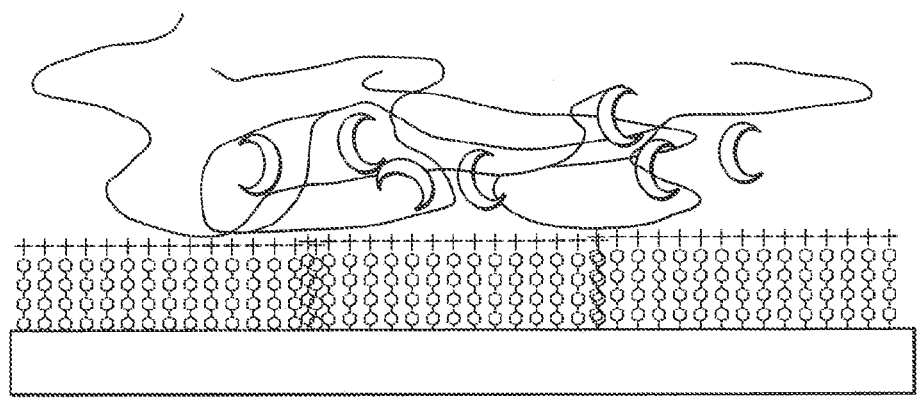
Figure 4D:
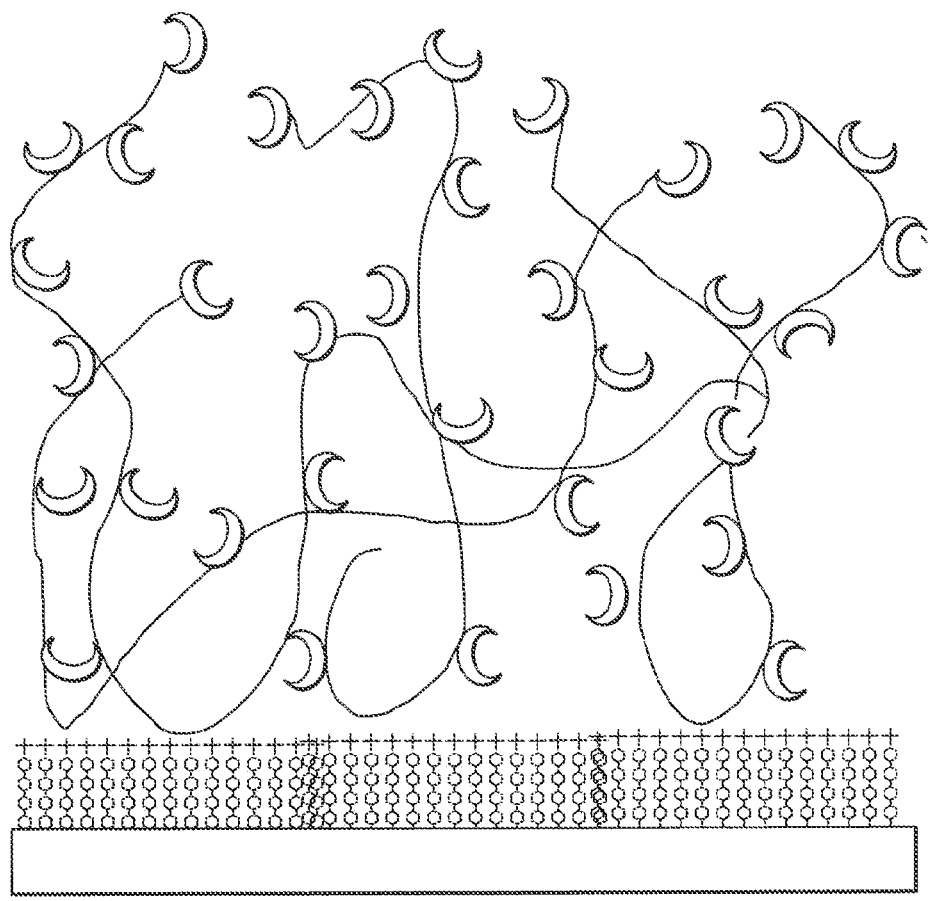

FIGS. 4a-4d illustrate the preferred embodiment ligand loading and linkage mechanism as follows. A hydrogel composed of extended chains (e.g., dextran) is attached to the linker film (SAM) using covalent coupling as illustrated in FIG. 4a. The hydrogel is preactivated to introduce coupling groups (e.g., NHS esters). Then self-associate these extended chains to form a cross-linked mesh as shown in FIG. 4b. Ligands (e.g., proteins) exposed (e.g., in solution) to this cross-linked hydrogel mesh will be entrapped mechanically, resulting in the accumulation of ligand within the hydrogel where it is covalently immobilized through reaction with the previously-introduced coupling groups; see FIG. 4c. Once the ligand is immobilized (coupled), the cross-linking of the hydrogel is reversed resulting in an extended hydrogel with a high density of immobilized ligand as depicted in FIG. 4d. Residual coupling groups in the hydrogel are blocked. Any techniques that reversibly cross-link the hydrogel may be employed. A cleavable covalent linkage, such as a sulfide bond between adjacent chains is suitable. But other noncovalent interaction may be more suitable for induction of reversible hydrogel cross-linking.

EXAMPLE 1

Activation of a hydrogel using N,N'-Carbonyl diimidazole (CDI) causes cross-linking of hydroxyls that in close proximity via an active imidazole carbonate. The activated surface is expose to a protein solution (0.1 mg/ml in phosphate buffer, pH 8.0) resulting in entrapment of protein molecules in the cross-linked hydrogel mesh. The active carbonate linkage reacts with the primary amines of the protein resulting in covalent coupling of the protein. Any remaining imidazole carbonates are inactivated using 1 M ethanolamine, pH 8.5. It is important to limit the contact time of the protein with the active surface to prevent excessive linkages with the hydrogel from forming.

EXAMPLE 2

The substitution of the amino acid histidine into a dextran hydrogel already having coupling groups introduces both amidazole and carboxyl groups. Then exposing the hydrogel to a buffer of pH<6.0 will result in the presence of both positive and negative charges that pair up and provide a cross-linking of the matrix. Protein in solution is then entrapped mechanically in the pores formed due to cross-linking and immobilized via the coupling groups already present. Then increasing the pH will undo this electrostatic cross-linking. More precisely, a cross-linked state is attained at pH<6.2 and a non-cross-linked state at pH>6.2.

EXAMPLE 3

The coupling groups may be carboxymethyl and the reversible cross-linking employs phenyl bis(boronic acid). This reagent interacts with adjacent hydroxyls on a hydrogel for pH in the range 8 to 9, thereby cross-linking any hydrogel possessing a cis-diol (e.g. dextran). After ligand entrapment and immobilization, the cross-linking interaction is reversed at pH in the range 3 to 4.

EXAMPLE 4

Cross-linking employs an affinity interaction such as metal chelating linkages where a metal ion receptor (e.g., imidodiacetic acid) and a poly-histidine tag are each linked to the hydrogel matrix. Then the presence of the appropriate metal ion (e.g., $Ni^{2+}$) will complex with the receptor and tag to form a crosslink. Whereas, introduction of a competitive metal chelating agent such as ethylenediamine tetraacetic acid or absence of the appropriate metal ion or changing the pH of the local environment reverses the complex formation, and hence, reverses hydrogel cross-linking.

Other coupling groups include reactive imidazole derivatives, epoxy, aldehyde, solfonyl chlorides, divinylsulfone, halogens, maleimide, dusulfides, and thiols. Other cross-linking groups include diols which are cross-linked by complex formation when exposed to molecules possessing two or more boronic acid residues. Other cross linking reversing methods include changing the ionic strength of pH or adding a cross-linking inhibitor.

4. Amorphous Iron Oxide Nanoparticle Amplification

The signal from an SPR sensor indicating target analyte bound to the immobilized ligands in the interaction layer can be amplified by a further step of introducing a second solution or colloidal suspension containing a second ligand which also binds specifically to the analyte and thereby increase the mass bound in the biointerface. That is, rather than just measure the refractive index change due to added analyte, measure the refractive index change due to added second ligand plus analyte. This is analogous to forming a sandwich of ligand1/analyte/ligand2 when analyte is present, and thus increases the sensitivity of the SPR sensor.

A preferred embodiment amplification method uses a second ligand linked to a nanoparticle of amorphous iron oxide ($Fe_2O_3$); this not only increases the bound mass but adds highly polarizable material to greatly change refractive index. For example, the target analyte could be an antigen, and the biointerface could include an immobilized first antibody to the antigen. Thus when a solution containing an unknown amount of antigen is introduced to the biointerface, any antigen will bind to the first antibody and thereby shift the resonance of the SPR sensor corresponding to the amount of bound antigen. Then, introduce to the biointerface a suspension of amorphous iron oxide nanoparticles (average diameter 5-100 nm) which have bound secondary antibodies to the antigen. The secondary antibodies (and thus the iron oxide nanoparticles) will bind to any (already-bound) antigen and thereby amplify the resonance shift of the SPR sensor. The resonance shift due to amorphous iron oxide nanoparticle plus second antibody plus antigen will be on the order of 100-1000 times the resonance shift due to the target analyte alone. Note that an antibody molecule may have size on the order of 10 nm, so many antibody molecules may be attached to a single iron oxide nanoparticle, especially when the constant part of the antibody links to the iron oxide to leave the variable part antigen-binding sites open. FIG. 5a heuristically illustrates this example of a sandwich of biointerface-antibody/antigen/antibody-iron oxide nanoparticle.

Further preferred embodiments protect the iron oxide nanoparticles with a coating of (short chain) carboxymethylated dextran which acts as a linker layer for the antibodies (or other analyte binding ligands). The carboxyl groups covalently attach to iron oxide, and the coating of dextran renders the surface stable in aqueous environments and resistant to nonspecific binding. FIG. 5b illustrates the coated nanoparticles with linked affinity ligands. The nanoparticles have a low density and sediment very slowly, and when coated with dextran the nanoparticles form a stable colloid in solution. Indeed, the nanoparticles typically are spongelike and porous and appear to be agglomerations of smaller particles on the order of 10 nm size. Other functional groups for covalently attaching to the nanoparticles may used in place of carboxylic; namely, thiol, hydroxyl, etc. And other materials may be substituted for the dextran to coat the nanoparticles; for example, other hydrogels that have minimal non-specific binding.

Because the iron oxide nanoparticles exhibit superparamagnetism, the nanoparticles can also be used to magnetically concentrate the antigen (analyte) prior to introduction to the SPR biointerface for measurement. That is, inject affinity-ligand coated amorphous iron oxide nanoparticles into a sample containing an unknown amount of analyte; next, pass the mixture through a magnetic field to extract the nanoparticles; and then introduce the extracted nanoparticles to the SPR sensor biointerface.

In more detail, a preferred embodiment amorphous iron oxide nanoparticle suitable for amplification may be prepared with the following steps:

(a) The amorphous iron oxide nanoparticles can be formed by sonication of $Fe(CO)_5$ at 20 KHz for 4 hours in a decalin (or other solvent) solution under an air atmosphere at 0° C. The nanoparticle size can be increased by increasing the carbonyl concentration.

(b) The particle may be coated with the ligand of interest by simply suspending the particles in 10 mM phosphate buffer, pH 7.4, containing 0.14 M NaCl and adding a solubilized ligand in the required molar excess. A molar excess of 10:1 ligand to particle is acceptable. The mixture is incubated at room temperature for 1 h and bovine serum album is then added to a final concentration of 1 mg/ml to block excess binding sites. Coated particles may be stored in this solution, containing 0.05% sodium azide as preservative, at 4° C.

(c) Alternatively, the particles may be pre-coated in a short dextran to improve performance and then link the ligand of interest. Suspend the particles in 10 mM phosphate buffer, pH 7.4, containing 0.14 M NaCl and add dextran at 1 mg/ml. The mixture is incubated at room temperature for 1 h. The coated particles may be recovered by centrifugation and resuspended in 10 mM phosphate buffer, pH 7.4, containing 0.14 M NaCl and 0.05% sodium azide as preservative. Ligand may be linked to the dextran coated particles using the appropriate linkage chemistry.

5. Amorphous Iron Oxide Nanoparticle Applications

The preferred embodiment amorphous iron oxide nanoparticles may also be used for enhancement of various assays. In particular, disposable test strip (lateral flow) devices where affinity recognition is visualized by the accumulation of colloidal particles in a localized area giving rise to a visible color intensity change at the area. In addition, these super paramagnetic preferred embodiment nanoparticles are ideal for all technologies employing super paramagnetic particles for magnetic separation of target analytes.

6. Systems

Figure 6:
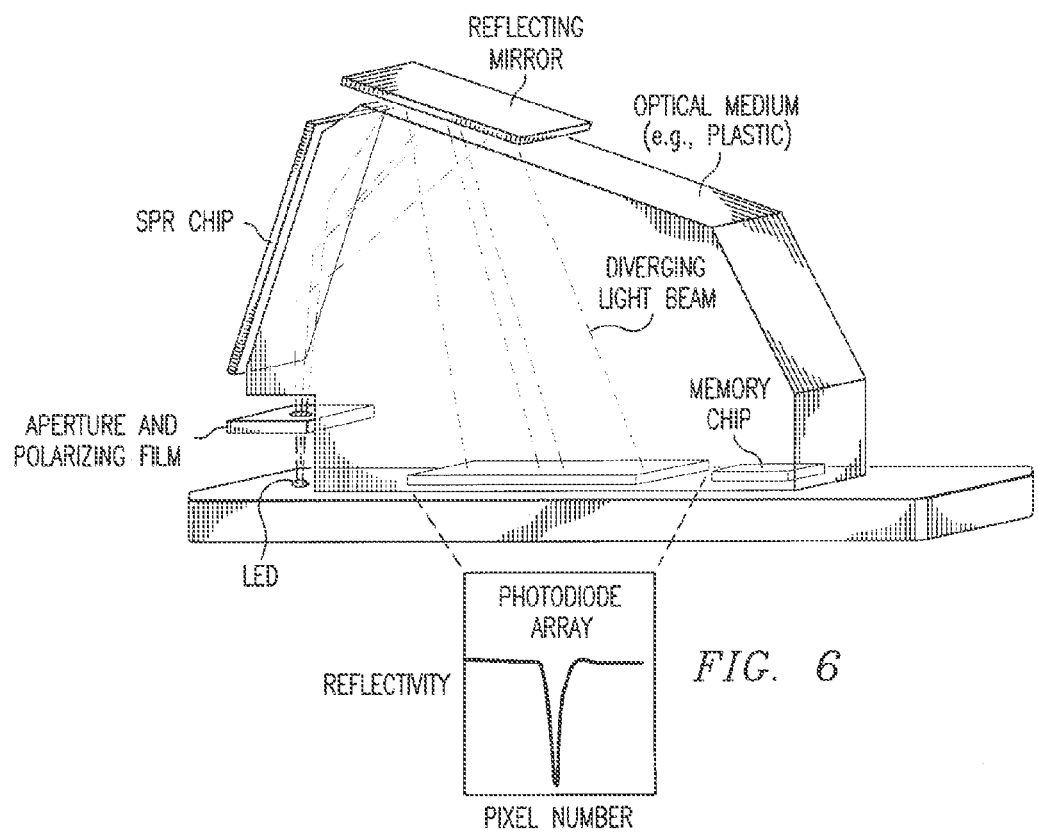
FIG. 6 is a cross-sectional elevation view of an SPR sensor.

Preferred embodiment SPR sensors have the overall structure as illustrated in FIG. 6 plus use a preferred embodiment biointerface as in the foregoing. Further, preferred embodiment ligand loading methods can be applied to either preferred embodiment SPR sensors or other SPR sensors with hydrogel interaction layers. Lastly, preferred embodiment iron oxide nanoparticle amplification or enhancement methods can be used in operation of either preferred embodiment SPR sensors or other SPR sensors with immobilized ligands or other assay systems using concentrations, visible or magnetic.

7. Modifications

The preferred embodiments may be modified in various ways while retaining one or more of the features of a biointerface with a linker film of rigid chains adjacent the surface and a method of interaction layer ligand loading and amorphous iron oxide amplification/separation.

For example, the SAM structure X—R—Y could be varied so that X could derive from any of thiol, disulfide, sulfide, selenide, diselenide, thiocarboxyl, and other such groups with a sulfur/selenium for binding to gold or other free electron metal; and X could include one carbon atom (such as a thiocarboxyl) connected to R; R could be any carbon chain with a rigid structure adjacent the metal and preferably linear; and Y could terminate in any convenient functional group(s), especially group(s) with a cross-sectional diameter comparable to the site spacing on the metal surface to provide a dense SAM surface.

What is claimed is:

1. A surface Plasmon resonance sensor structure for sensing a target analyte, comprising:
    a metal sensor film having a metal surface,
    a biointerface comprising a monolayer bound to said metal surface, said monolayer formed from a plurality of units, said plurality of units including units with the structure XR—Y wherein:
    (i) X is selected from the group consisting of —S—, —S—S—, —Se—, —Se—Se—, —S—Se—, and mixtures thereof where "—" indicates a chemical bond;
    (ii) R is a carbon backbone of chain length of at least 6 carbon atoms including double or triple bonds along said chain length; and
    (iii) Y contains a functional group at a surface of said monolayer,
    wherein said target analyte is bound to said functional group, and
    a plurality of amorphous iron oxide nanoparticles having at least one ligand attached thereto that has structure for binding to said target analyte, wherein said ligand is bound to said target analyte,
    wherein said functional group of said Y is selected from a group consisting of tris-hydroxymethyl ethyl groups, gem-ethyl diol, fluoro gem-propyl diol, and ethylamide.

2. The structure of claim 1, wherein:
    (a) said R is selected from the group consisting of aromatic rings, aromatic rings paraconnected by linear alkynes, and direct paraconnected aromatic rings.

3. The structure of claim 2, wherein the direct para-connected aromatic rings are biphenyl.

4. The sensor structure of claim 1, further comprising a hydrogel coating covalently attached to said plurality of amorphous iron oxide nanoparticles and being between said plurality of amorphous iron oxide nanoparticles and said ligand.

5. The sensor structure of claim 4, wherein said hydrogel coating comprises a carboxymethylated dextran layer.

* * * * *